United States Patent [19]

Thompson et al.

[11] Patent Number: 4,644,943

[45] Date of Patent: Feb. 24, 1987

[54] BONE FIXATION DEVICE

[75] Inventors: Roby C. Thompson, Minneapolis; Arthur G. Erdman, New Brighton; Frank D. Dorman, Minneapolis, all of Minn.

[73] Assignee: Regents of the University of Minnesota, Minneapolis, Minn.

[21] Appl. No.: 632,851

[22] Filed: Jul. 20, 1984

[51] Int. Cl.⁴ .............................................. A61F 5/04
[52] U.S. Cl. ........................... 128/92 YY; 128/92 YJ; 128/92 VD
[58] Field of Search ............. 128/92 BC, 92 D, 92 E, 128/92 R, 92 B, 92 BB, 92 BA

[56] References Cited

U.S. PATENT DOCUMENTS

| | | | |
|---|---|---|---|
| 3,670,724 | 6/1972 | Bosacco | 128/92 D |
| 3,793,650 | 2/1974 | Ling et al. | 3/1 |
| 3,829,904 | 8/1974 | Ling et al. | 3/1 |
| 3,900,025 | 8/1975 | Barnes, Jr. | 128/92 D |
| 3,986,504 | 10/1976 | Avila | 128/92 |
| 4,098,269 | 7/1978 | Judet | 128/92 |
| 4,119,092 | 10/1978 | Gil | 128/92 D |
| 4,262,665 | 4/1981 | Roalstad et al. | 128/92 BC |
| 4,277,197 | 7/1981 | Bingham | 403/104 |
| 4,281,649 | 8/1981 | Derweduwen | 128/92 BC |
| 4,289,124 | 9/1981 | Zickel | 128/92 D |
| 4,300,418 | 11/1981 | Gusching et al. | 82/36 |
| 4,308,863 | 1/1982 | Fischer | 128/92 |
| 4,360,012 | 11/1982 | McHarrie et al. | 128/92 |
| 4,364,382 | 12/1982 | Mennen | 128/92 |
| 4,373,518 | 2/1983 | Kaiser et al. | 128/92 |
| 4,416,278 | 11/1983 | Miller | 128/305 |
| 4,502,160 | 3/1985 | Moore et al. | 128/92 BC |

FOREIGN PATENT DOCUMENTS

| | | | |
|---|---|---|---|
| 96695 | 10/1978 | Poland | 128/69 |
| 1009444 | 4/1983 | U.S.S.R. | 128/92 E |

Primary Examiner—Robert P. Swiatek
Assistant Examiner—C. W. Shedd
Attorney, Agent, or Firm—Kinney & Lange

[57] ABSTRACT

A bone fixation device for securing adjacent and separated bone portions, such as at a joint or at a relatively clean, unsplintered break, comprises a pair of telescoping members which are pinned into the respective bone portions, and have internal actuating members to permit the telescoping parts to be moved together to bring the two bone portions to bear against one another at a desired level of pressure. After the telescoping members have been adjusted the members are permanently left in place to fix and hold the joint or break in a predetermined relationship. The adjusting members also remain in place as pins within the bone, which are accessible through incisions in the skin if later adjustment is necessary. The entire device is embedded, and is not external. The process of inserting is relatively simple to follow and rigidly fixes a joint or break between two abutting bone portions without having external members.

14 Claims, 14 Drawing Figures

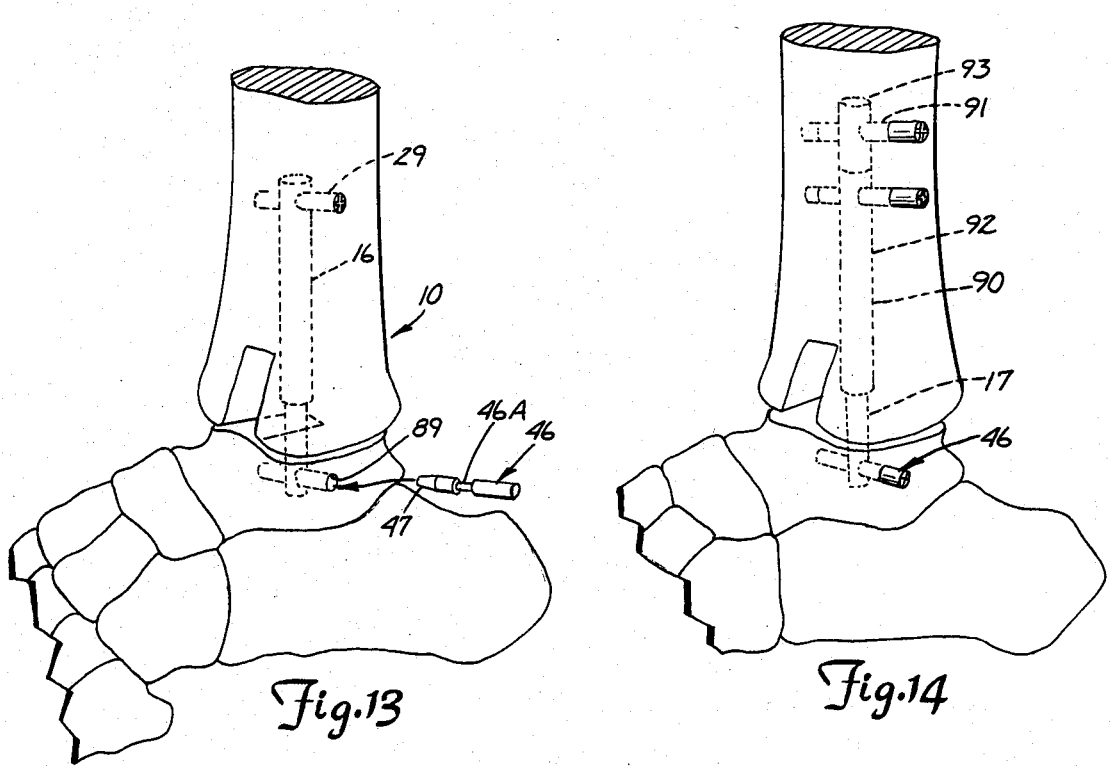
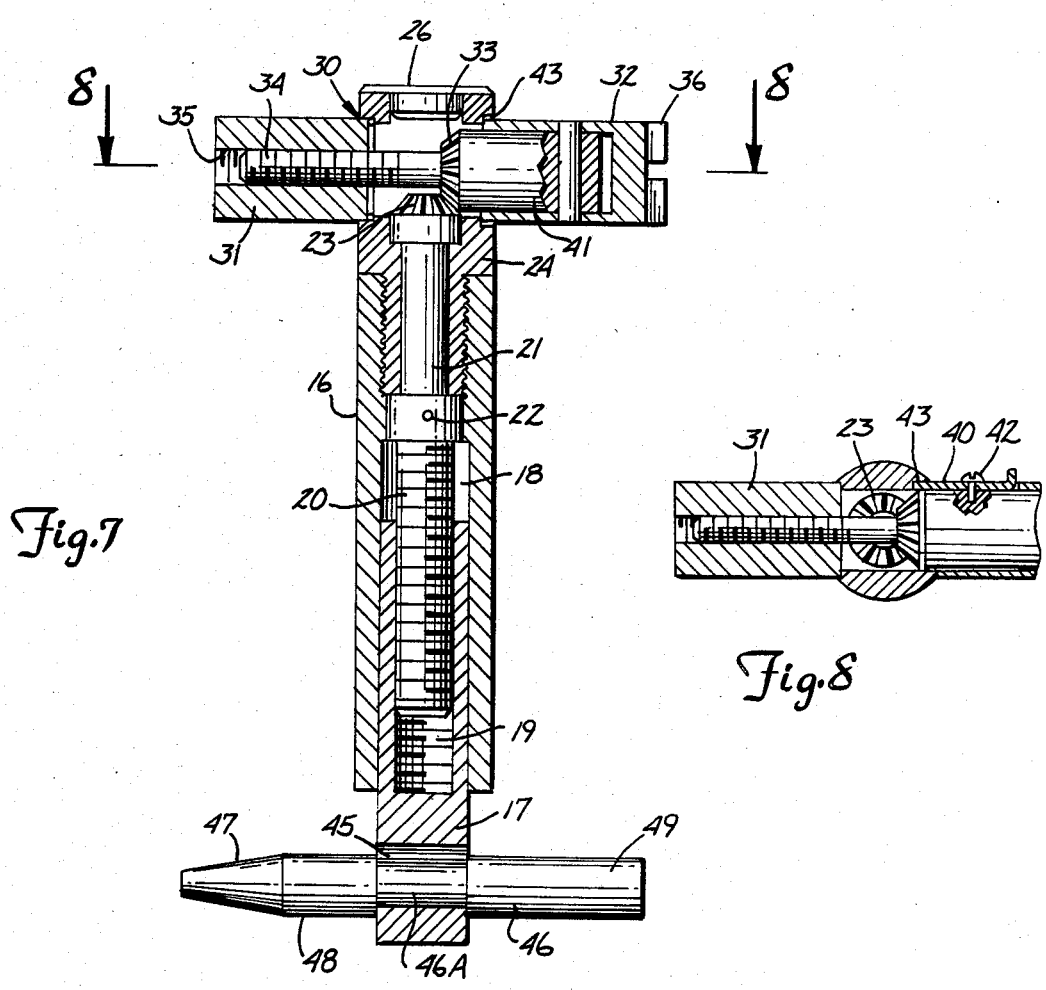

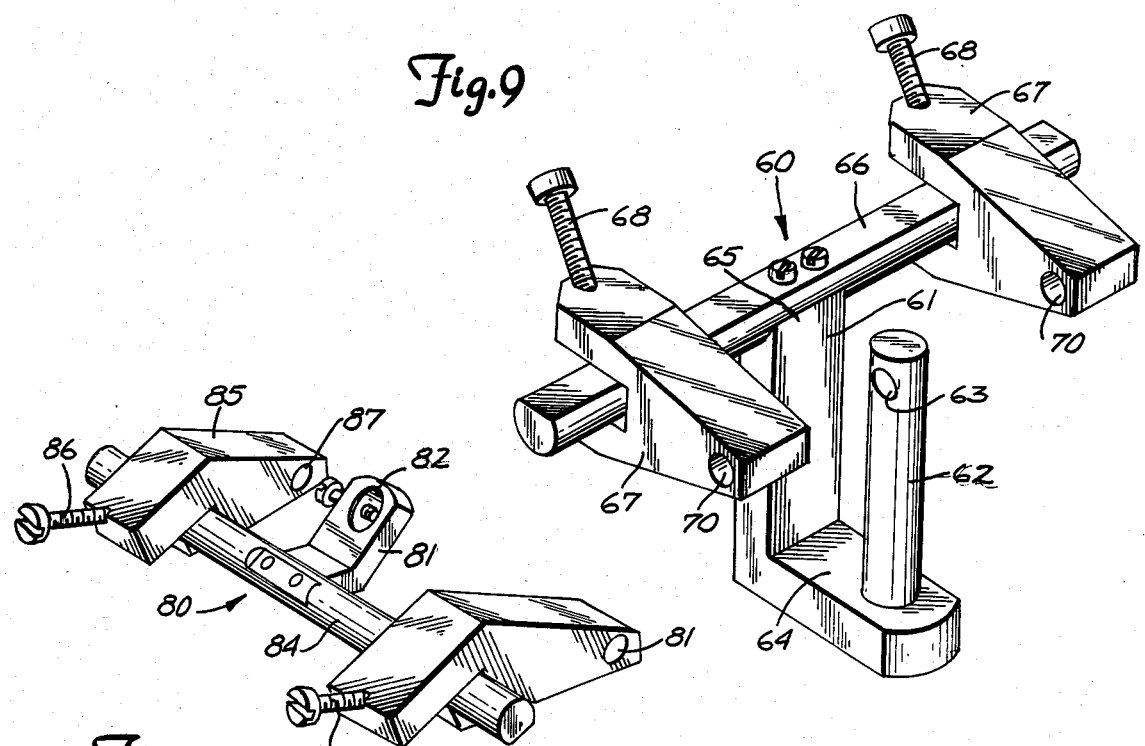
Fig. 9
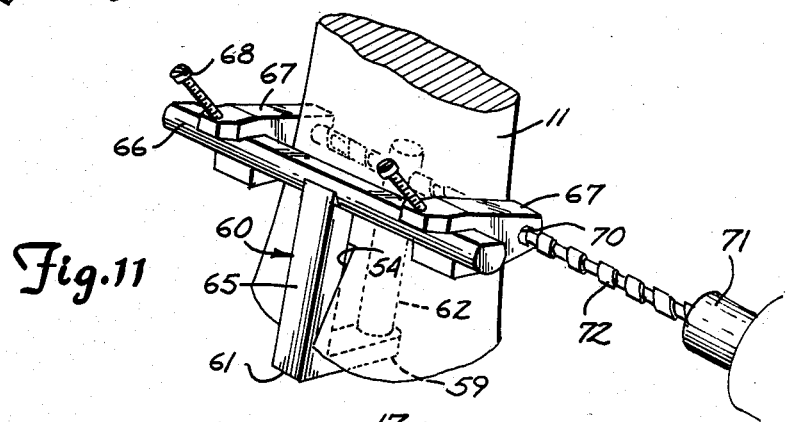
Fig. 10
Fig. 11
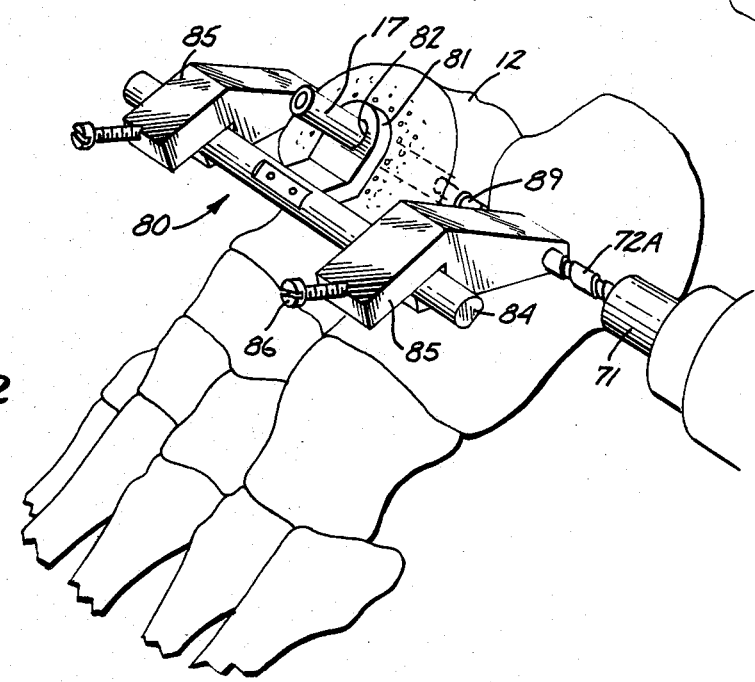
Fig. 12

BONE FIXATION DEVICE

BACKGROUND OF THE INVENTION

1. Field of the Invention.

The present invention relates to a fixation device for immobilizing two portions of a bone at a joint, which may be a natural joint or a fracture.

2. Description of the Prior Art.

Various fixation devices for securing two segments of fractured bone, or for immobilizing a normal joint have been advanced.

The most common technique currently used for influencing fusion between two bone segments is to employ an external frame attached to pins that have points engaging the bone above and below the joint. The pins protrude through the skin and are fixed to clamps that can be compressed one against the other through the external device. The external fixation device is associated with a bulky external frame which may create problems with the opposite limb. In addition, complications of infection around the pins which protrude through the skin can be major problems. Internal fixation with screws across the joint is also used, but the screws do not allow for the bone segments to settle against each other as resorption of bone occurs and, therefore, may end up distracting the two bones as time goes on.

U.S. Pat. No. 3,986,504 shows an internal fixation device for securing two fractured bone joints together. This is a elongated probe having an outer sheath that is driven through the end of the bone that is broken (it appears that it has to be a large bone for use). After the sheath has been driven to span the break sufficiently a screw thread member that is on the interior of the outer sheath is actuated causing pins to be spread out to grip the bone, and the screw tends to pull the joint together.

Use of the device appears to cause excessive trauma, and because the location of the inserted part is dependent upon alignment of the sheath when it is initially pounded into the end of the bone, it would tend to be difficult to use.

Typical external fixation devices are sold by Howmedica, Inc. of Rutherford, N.J. Large external fixation frames sold under the trademark HOFFMANN are provided for the ankle and knee and other portions of the body. The frames are very awkward, because they are large, bulky, and tend to be bumped, and will catch on things if the patient is mobile. Additionally, the devices incorporate probes or pins that pass through the skin causing points of potential infection. The pins are difficult to fix tightly so that there is a tendency of the pins to slip when in use.

A device very similar to devices sold by Howmedica, Inc. is shown in U.S. Pat. No. 4,360,012. It comprises a large external frame that is placed on the outside of the body and forms a splint for fixing fractures. Another external fixation device is shown in U.S. Pat. No. 4,308,863. This patent also shows the typical use of external frames having transfixing pins that are positioned against the bone and pass through the skin and tissue to reach the bone. Again, the pins pass through the skin, which are locations susceptible to infection.

An articulated external fixation device is shown in U.S. Pat. No. 4,098,269 operating on the same principle except that the pins shown are actually screwed into the bony part to be immobilized. While this tends to hold the pins in place, the screw pins can irritate adjacent tissue and may come loose, and of course the pins still have to pass through the skin, which provides a scource of infection. Further, if the pins are not screwed in correctly, there is a chance of bumping the device and further damaging the bone where the pins enter the bone.

An internal fixation device for bone fractures is shown in U.S. Pat. No. 4,364,382. It is a metal plate that has edge fastening formations on two edges that will tend to secure the bone fracture site by deforming the plate so it penetrates into the bone and bridges the bone fracture. The plate fits over the bone, so that it is not within the bone, but it is beneath the skin.

Drilling and cutting bones with various devices has been known in the past as well. For example, U.S. Pat. No. 4,373,518 discloses a method of drilling live bone, and U.S. Pat. No. 4,416,278 illustrates a bone plug cutter that will permit cutting a plug of bone for implanting a prosthesis. Its primary use is in hip arthroplasty.

A prosthetic bone joint for hip reconstruction that is inserted into the bone canal or bore and which has means for centering it in the bore is shown in U.S. Pat. No. 3,793,650. This centering device is for insuring that the stem that goes into the bore is centered so that cement will surround the part and hold it securely.

A hip joint prosthesis is shown in U.S. Pat. No. 3,829,904, and this also utilizes a device with a stem that fits into the interior canal of a bone.

Various telescoping members have been advanced. For example telescoping tools and couplings are shown in U.S. Pat. No. 4,277,197, and a tool turret mechanism having telescoping parts is shown in U.S. Pat. No. 4,300,418. However, these devices are merely of general interest to show that telescoping members have been known, but have nothing to do with reconstruction of bone joints.

SUMMARY OF THE INVENTION

The present invention provides an internal mechanical device to constrain two bones or bone portions in contact with each other for a long enough period of time for a union to occur between the two bones or bone portions. Primary usage and utility is for fixation of a human bone joint that requires fusion of the joint as a result of deterioration or some disease process. The mechanism comprises a pair of members which are axially movable relative to each other and preferably telescope. A separate member is inserted into each of the adjacent bone portions on opposite sides of the joint or break. The possibility also exists for distracting the two bone fragments such as in lengthening a bone. This could be accomplished by initiating the implant at its shortest length and then lengthening as indicated with time.

The openings for the relatively movable members are precisely located with jigs, and cross bores spaced from the joint or break are provided in each of the bone portions. When the elongated members are telescoped together and inserted into the provided longitudinal bores, cross pins are inserted in the cross bores in the respective bone portions. The cross pins also pass through cross bores in the ends of the elongated members to secure the elongated members from longitudinal movement relative to the bores.

One of the cross pins is a fixed pin that provides an anchor, while the other cross pin includes a mechanism for actuating the two telescoping members in a manner so that they will be drawn together in longitudinal axial direction to move the two bone portions together so that the abutting joint or break surfaces will be held mated under a desired compressive load. The actuating mechanism is then locked to maintain the desired load on the joint or break, and the wound is closed.

The entire device, including the cross pins is subcutaneous, and thus there are no locations where pins will exit the skin and result in infection. Additionally, the adjustment devices can be operated subsequent to installation by making the cross pin accessible by an incision in the skin to adjust the compression of the two bone portions to maintain the bone portions under sufficient load, or at least in contact, to permit adjustment for bone resorption at the joint or break.

By following a process for locating jigs for forming the cross bores in which the anchoring pins will be placed, the parts are very precisely positioned and will provide adequate compression to insure adequate bone fusion at the joint or break. The device can remain in place, and once bones are fused or healed there is no need to remove the parts.

BRIEF DESCRIPTION OF THE DRAWINGS

FIG. 7 is a vertical sectional view of the bone fixation device of the present invention showing the internal working details;

FIG. 8 is a fragmentary sectional view taken as on line 8—8 in FIG. 7;

FIG. 9 is a perspective view of a first jig used for locating the cross bores necessary for securing the device of the present invention;

FIG. 10 is a perspective view of a second jig for locating the second cross bore on a second bone portion;

FIG. 11 is a perspective view showing the jig of FIG. 9 in position and in use;

FIG. 12 is a perspective view showing the second jig shown at FIG. 10 in use;

FIG. 13 is a perspective view of a joint with the device of the present invention partially installed; and FIG. 14 is a perspective view showing a modified form of the present invention utilizing two pins in an upper portion of the bone fixation device of the present invention for additional anchoring capabilities.

DETAILED DESCRIPTION OF THE PREFERRED EMBODIMENTS

Figure 1:
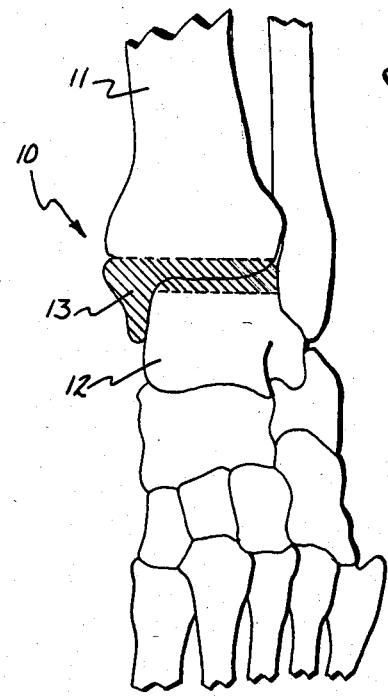
FIG. 1 is a perspective view of a typical ankle joint that is to be repaired with the device of the present invention and with the area of diseased bone to be removed shown shaded.

The present invention and its use is illustrated in connection with the fixation of the ankle joint. Specifically, the joint between the lower end of the tibia, and the upper side of the talus is shown being treated. As shown, a human ankle joint indicated generally at 10 is to be immobilized. The tibia 11 and talus 12 are uncovered surgically and diseased sections 13 are removed from the adjacent surfaces with a surgical saw so that there are relatively flat facing surfaces such as those shown at 11A and 12A in FIG. 2.

The device of the present invention is illustrated generally at 15, and in particular in FIGS. 4, 5, 6, 7 and 8. Comprises a pair of cylindrical members, comprising a first elongated outer housing member 16 and a longitudinally telescoping shaft 17. The lower end of the member 16 is tubular so that the shaft 17 will telescope up into the member 16, as shown generally in FIG. 5. The shaft 17 slidably, securely telescopes into the housing so the two parts resist side to side flexing.

The detail of the interior construction of the device 15 is shown in FIG. 7, and as can be seen the housing 16 is formed to have a elongated interior chamber 18 at its lower end which slidably and closely receives the lower shaft member 17. The interior of the shaft 17 has a bore or chamber indicated at 19 that is threaded to receive the end of a screw 20 which is rotatably mounted on the interior of the housing 16.

The screw 20 is suitably rotatably supported in the housing 16, and is pinned with respect to a drive shaft 21 with a pin 22. A collar 22A forms a support for rotation of the screw. An end tab of the drive shaft fits into the collar and is pinned in place. The opposite end of the drive shaft 21 has a gear 23 formed thereon, and a removable gear support 24 is threadably mounted on the interior of the housing 16 at one end to permit assembly of the parts. The gear 23 is securely held in its proper location. The upper end of the bore 18 in which the gear housing 24, gear 23 and screw 20 are mounted is closed with a suitable plug 26.

The upper member or housing 16 has a cross bore indicated generally at 30 therein, and when fully assembled, cross bore 30 mounts a cross pin assembly 29 comprising a first cross pin section 31 extending laterally from one side of the bore 30 and thus from one side of the housing 16, and a second drive cross pin section 32 which extends out the opposite end of bore 30 from cross pin section 31. The drive cross pin section 32 supports a gear 33 which meshes with the gear 23 when the pin sections 31 and 32 are in proper position. The pin sections 31 and 32 are held together in assembly, and in the form shown the sections are held together with a longitudinal threaded rod 34 on pin section 32 that threads into a bore 35 in the pin section 31.

The outer end of the cross pin section 32 has a drive slot 36 to permit using a screw driver for rotating the pin section 32, thereby driving the gear 33, and thus gear 23 to rotate the screw 20.

Additionally, as shown in FIG. 8, as one example of a lock to prevent reverse rotation, the outer portion of the cross pin section 32 has a rotation locking device comprising a flat section defined thereon with a small lock tab 40 slidably mounted on this section and retained for sliding movement with a pin 42 so that the lock tab 40 can be slid axially along the pin section 32 to engage a provided recess or notch in housing 16 shown in FIG. 8. Several recesses may be arranged around the outer periphery of the cross bore 30 on the side of the cross bore from which pin section 32 extends so that once the pin section 32 is in its proper rotational position for locating the telescoping shaft 17, the lock tab 40 can be actuated to hold the screw 20 from reverse movement, which would tend to loosen the joint that is being fixed. Other types of locks may also be used as desired.

The telescoping cylindrical shaft 17 has a cross bore 45 defined therein adjacent one end, which is of size to receive a unitary fixed cross pin 46 when the device 15 is in position in the bone portions that are to be held together. Pin 46 has a tapered end 47 on a first pin section 48 that extends laterally from one side of the telescoping shaft 17, and a second pin section 49 extends from the other side of the shaft 17. The pin sections are joined by a necked down center section 46A.

Figure 2:
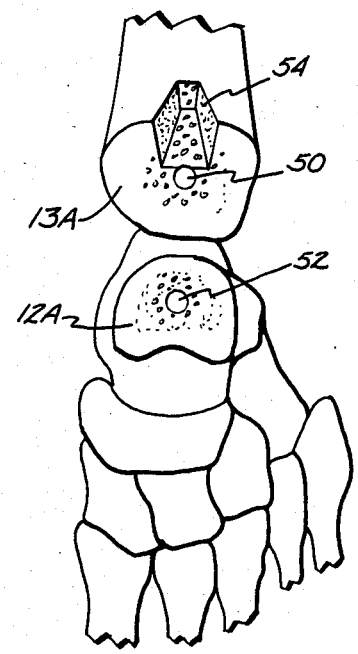
FIG. 2 is an illustrative example with the joint separated to show installation openings for the device of the present invention.

The process of installation, once the joint has been prepared as previously explained, and as shown in FIGS. 1 and 2, is to first drill a longitudinally extending hole or bore indicated generally at 50 into the tibia. The bore 50 is centered in the tibia, and this centering can be done by sight, in that the center canal of the bone can be quite easily identified, and then a conventional surgical drill can be held parallel to the axis of the bone for drilling. The bore 50 is drilled to receive the tubular housing 16 quite snugly, and is drilled of sufficient length so that the housing 16 will be completely recessed within the bone portion when it is installed in the bore.

Next, a suitable marker, such as a conventional center point marker member used for locating dowel pins, or some similar marker, would be placed in the bore 50 and the talus repositioned in the desired location on the talus for alignment purposes. This will leave a mark in the location where the bore 50 meets the talus, and then a second bore 52 is formed in the talus, of sufficient depth to accomplish the seating of the telescoping shaft 17 so that the cross bore of shaft 17 will be well below the surface 12A, but not so far as to pass completely through the talus and into the lower part of the heel.

Once these bores 50 and 52 have been made, jigs will be used for providing cross bores in the bones to be fixed, and in the particular instance shown, the jig used with the tibia requires the removal of a small portion of bone adjacent the front of the tibia. To accomplish this, a suitable series of saw cuts will be made to form a slot indicated generally at 54 in the front of the tibia. The slot serves to steady the jig, and other cuts in the bone may be made to adequately stabilize the jig for accurate boring. This can also be seen in FIG. 3, and is used for clearance of the jig that is used as well as steadying it, as will be explained.

In FIGS. 9 through 12, the jigs used for precisely locating the cross bores in the bone portions that are joined together are shown. This precise location of the cross bores is important in making sure that the parts will fit together well, that the bone joints will be mated properly and that the cross pins will be supported in the respective bore portions on both sides of the longitudinally extending bores 50 and 52. In other words, because the cross bores are quite precisely sized it is important that no undue stress be placed on the bones when the cross pins are inserted, and that adequate support is provided. The jigs precisely locate and align the needed bores so no "bad holes" are formed as may occur with freehand techniques. The precision jigs provide the advantages of a minimum amount of bone removal for the apparatus.

FIG. 9 illustrates a first jig 60 which is used for drilling the cross bore in the tibia in the form shown, and while the jigs are shown for the particular joint shown, similar jigs are used for repairing a break of an individual bone where the fixation device is to be used. The jig must be properly seated in the bore of the bone portion in which the particular fixation device section is to be placed, so the drill pilot bushings for drilling the respective cross bore are accurately located.

The jig 60 includes a frame 61 that is L shaped and which has a base 59 on which a center pilot pin 62 is fixed in a suitable manner. The pin 62 is precisely sized to fit into the bore 50, and includes a pilot hole 63 therethrough at one end which is also the same size as the cross bore that is to be made. The pin 62 simulates the housing 16 in size, and is slightly longer than the housing 16 so that when the cross bore is formed it will be located so the housing 16 will be recessed into the bone section slightly.

The base 59 of frame 61 has a reference surface 64 which will fit against the end surface 11A of the bone portion 11 when the pin 62 is slid into the bore 50, and the upright member 65 of the frame 61 will be positioned in the slot 54 as shown at FIG. 11 when it is inserted into the tibia 11. The upright member 65 has an upper surface that supports a cross beam 66 that extends laterally and spans the tibia 11 as shown in FIG. 11. A pair of pilot arms 67 forming drill pilot bushings are adjustable along the cross beam and held in place with suitable set screws 68 that are provided in each of the arms.

Each of the arms 67 has an outer end portion in which a pilot bore 70 is formed. When in place on the tibia, as shown on FIG. 11, the pilot bores 70 will be precisely aligned because the set screws 68 will position the arms 67 on the cross beam 66 identically, and the arms 70 can be placed tightly against the sides of the bone 11.

During the procedures for inserting the fixation device into the bone, tissue will be separated to permit the jigs or fixtures to be put into place. The tissue and tendons in the ankle area can be moved adequately to permit clearance for these operations. Once the first jig 60 is in position, a surgical drill indicated generally at 71 having a suitable size bit 72 will be piloted through the pilot bore 70 of one of the arms 67, as the frame 61 is held securely in place with the surface 64 abutting the end of the tibia which had been previously cut flat to provide the plane surface 11A.

The drill bit 72 then is moved through the pilot bore 70, and drilled into the first bone portion that is being fixed relative to the other bone portion. The drill bit 72 is moved all the way through one side of the bone and into the pilot bore 63 of the pin 62 and through the other side of the bone on the opposite side of the bore 50, until the drill bit pilots in the pilot bore 70 on the opposite arm 67 all the way across the tibia 11. The cross bore is drilled to its precise size and it is precisely positioned by the use of the jig including the pilot bores 70 and 63. The drill bit can then be removed, and the first jig 60 removed from the tibia.

A second jig 80 shown in FIGS. 10 and 12 is used for drilling into the talus, or the second bone portion. The second jig 80 has a frame 81 which has a center bore 82 into which the actual shaft member 17 may be mounted. As shown, the shaft 17 is mounted and held securely in the bore 82, as shown in FIG. 12, through the use of a set screw 83. The surface of frame 81 defining the bore is of sufficient length to properly position the shaft 17 and hold it securely.

A cross beam 84 is mounted on the upper end of the frame 81, and this cross beam 84 in turn provides support for a pair of arms 85, that have slots to receive the cross beam. Set screws 86 are used for fixing the arms 85 in position on cross beams 84. The arms 85 have outer end portions that are suitably positioned to locate pilot bores 87 in proper location in relation to the bore 45 of the shaft 17 when the shaft is installed in the bore 82. The shaft 17 is located before it is fixed into position by running a drill bit 72A through the pilot bores 87 and the bore 45 prior to placement on the talus, and then fixing the set screw 83 tightly to hold the shaft 17 in position. The drill bit 72A is then removed. The drill bit 72A may be a different size than drill bit 72.

The second jig 80 is placed into position on the talus by sliding the previously positioned telescoping shaft 17 into the bore 52 that previously had been formed, and adjusting the arms 85 laterally so that they are tightly against the sides of the second bone portion (comprising the talus in this disclosed form) and clamping the arms into position with the set screws 86. The surgical drill 71 is used to move the drill bit 72A through one bore 87, through the bone and into the bore 45, and then across the bone into the other pilot bore 87 on the opposite arm 85. Once the cross bore has been drilled, then the drill bit 72A will be removed.

If desired, the arm 85 on the far side of the bone may be removed from the cross beam 84 and the drill bit 72 backed out. The cross pin 46 inserted through one side of the bone bore 89 in the talus and through the cross bore 45, and then through the other side of the bone bore as the drill bit is removed to secure the shaft 17 in place. The set screw 83 would be released to then permit the jig 80 to be slipped off the shaft and removed.

The telescoping shaft 17 may be removed from the bone with the jig and later reinserted, if desired.

In the installation procedure, the housing 16 may be inserted into the bore 50 of the tibia or first bone portion, and then the cross pin sections 31 and 32 are inserted through the cross bore sections that have been formed in the bone, which align with the bore 30 in the housing 16. Depending on the amount of clearance for manipulation available between the bone portions, the housing 16 may be inserted, and then the upper cross pin sections 31 and 32 put into position so that the gears 33 and 23 are in mesh and driving relationship. The cross pin sections can be inserted through incisions in the skin that were made for running in the surgical drill, and the housing 16 will then be held in position because the cross pins are positioned in the cross bores in the bone.

The shaft 17 then can be inserted into the opening or bore 18 of the housing 16 (it may be initially left there as well) and is threaded to engage the screw threads in the shaft bore with screw 20. With the shaft 17 in the bore 52, and the threads on the interior of the shaft 17 started on the screw 20, the axial position of the shaft 17 can be adjusted by rotating the cross pin section 32 about its axis and driving the gear 33 and gear 23 to rotate the screw 20.

Figure 3:
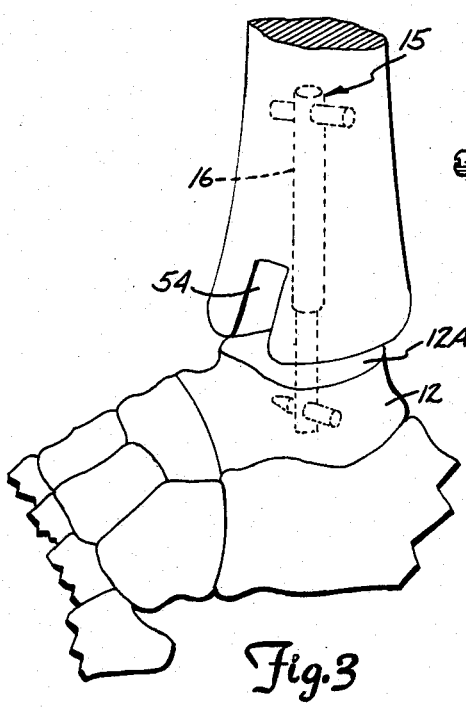
FIG. 3 is a perspective view of the joint of FIG. 1 shown with the device of the present invention installed therein.
Figures 4, 5, 6:
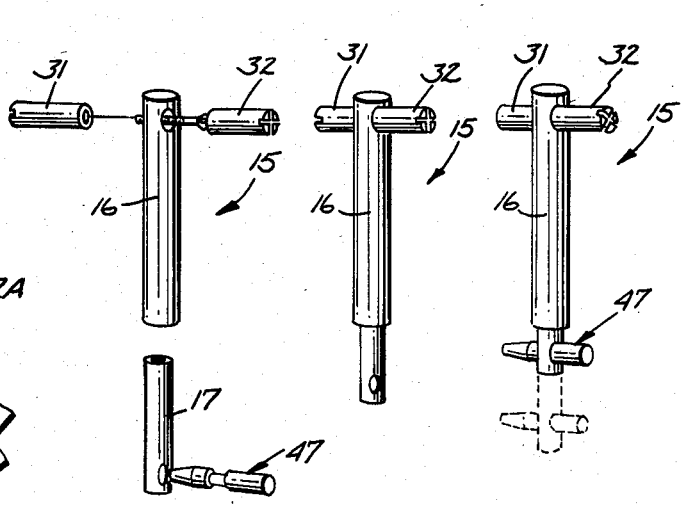
FIGS. 4, 5 and 6 are perspective views of the bone fixation device of the present invention in different stages of assembly.

The shaft 17 will be properly positioned longitudinally with the pin 46 in place through the bore 89 in the talus 12. The alignment of the shaft member 17 with the cross bore for pin 46 is aided by the tapered end 47 because the pin will tend to enter the bore 45 even if the shaft 17 is not precisely aligned initially. The cross pin is inserted through suitable incisions in the skin and moved until it is in position where the center section or neck portion 46A is in bore 45. As stated, this insertion of the pin 46 may occur before the jig is removed after drilling. When the fixation device is in position generally as shown in FIG. 3 with the end surfaces of the two bone portions spaced apart slightly, and the insertion step is shown generally in FIG. 13, wherein the pin 46 is positioned aligned to permit insertion into cross bore 89 in the talus.

The pin section 32 is then rotated more to cause screw 20 to pull the two bone portions together, generally as shown in FIG. 13, until the surfaces 12A and 11A are contacting. A sufficient pressure or compression on this joint or interface is exerted by the adjustment of the screw drive. The pin section 32 then can be locked in place with the sliding lock 40 or other suitable locking devices to prevent reverse rotation and loosening of the joint. The term "joint" as used in this specification means any interface between two bone portions, whether a natural joint or a break or fracture.

Additional fastening devices may be used, as shown in FIG. 14. A modified form of the fixation device is shown at 90 in place in a leg bone and includes not only the cross pin assembly of the previous form, but also an additional cross pin indicated generally at 91 that would be on an upper section 93 of the housing at 92 that is similar to the housing section 16. This upper section 93 provides a bore for receiving pin 91 and could be fastened in place. The cross bores are formed in the bone in the manner previously described, so that the housing 92 is precisely held with two cross pins, if this was deemed necessary. The lower shaft 17 could remain the same as it was in the previous form of the invention, including the cross pin 46.

If bone resorption occurs, which does generally occur when pressure is not maintained on a joint, the surgeon can check the condition of the joint and make an incision for access to the slots 36 on the pin section 32. After releasing the lock member 40, the joint can be tightened up by rotating the cross pin section 32. The amount of compression can be adjusted and maintained so that too much or too little compression is not a problem.

The positioning of the cross pins for the joint fixation device is accurate, and only affects the bone sections that are desired to be held together. For example, in previous methods of fusing the joint between the talus and tibia, a pin had been inserted through the bottom of the foot, and it fixed two joints, which immobilized the heel completely. The present device fixes only the joint between the talus and the tibia independently of any other joints in the foot. The positioning of the present device is accurate in the method used because jigs properly and precisely position the cross bores, and the device is lightweight and totally implantable so that there is no external members to interfere with movement or cause infection where they penetrate the skin. The compressive forces across the joint between the two bone portions can be adjusted and maintained, and the number of cross pins or cross pieces for holding can be varied to suit the needs for strength. The multiple cross pins can be in either or both of the sections, although FIG. 14 shows mutiple cross pins only in the housing 92. The fixation device need not be removed after the joint has fused.

The summary of the steps of use of the present bone fixation device includes cutting the ends of the bone at the joint (whether a normal joint or a break) and drilling a bore in one of the bone portions axially along the bone; preferably marking the bore location on the other bone portion where the bore for the elongated fixation device is to be made; forming a second bore in longitudinal direction on the second bone portion; forming any necessary clearance slots or jig guide slots in the bone for jigs and fixtures to be used; placing the jigs on the respective bone portions in sequence and piloting drill bits into the guides on the jigs to form a separate cross bore in each bone portion; inserting each part of the telescoping bone fixation device into the appropriate bone portion and inserting cross pins to hold them in place; placing the driving parts for the two telescoping portions together and drivably coupling them; moving the telescoping parts together so that the bone portions will move together and be held at a desired compressive load; and locking the drive so that the drive will not reverse and tend to loosen the joint formed between the bones.

The incisions that are made are then sutured closed to prevent infections, and the fixation device is left in place. It can later be adjusted as desired.

In the bone portion that does not have the gear drive, as stated after drilling only one side of the jig 80 need be removed so that the cross pin can be slid into place through the bone bore 89 with the jig still in place. The fixed cross pin has a reduced neck that detents into place on the shaft 17. The jig or fixture can then be removed by loosening set screw 83 while shaft 17 remains in bore 52.

The axial movement of the two members 16 and 17 toward or away from each other may be accomplished with other drives, such as gear means comprising a pinion gear driven by cross pin assembly 29 and a driven rack connected to shaft 17, which would comprise a rack and pinion gear drive.

Although the present invention has been described with reference to preferred embodiments, workers skilled in the art will recognize that changes may be made in form and detail without departing from the spirit and scope of the invention.

What is claimed is:

1. A bidirectional, adjustable fixation device for securing adjacent, separated bone portions together at an interface, and being completely implanted within such bone portions comprising:
    first and second longitudinally extending members adapted to be moved toward and away from each other along a longitudinal axis;
    said first member being adapted to be fitted into a provided longitudinally extending opening in a first portion of a bone to be secured to the second portion of bone, and said second member being adapted to be fitted into an aligning longitudinally extending opening of the second bone portion adjacent the interface of the bone portions to be fixed together;
    means within the bone portions to fix the first and second members relative to the respective bone portion against movement in direction toward the other bone portion;
    drive means mounted within the bone portions coupled between the first and second members so that upon actuating said drive means the first and second members will be moved axially relative to each other; and
    selectively actuatable actuating means substantially contained within one of said bone portions and extending through a transverse opening in said one bone portion for actuating said drive means from a position proximate the exterior surface of said one bone portion.

2. The adjustable fixation device of claim 1 wherein said drive means includes gear means in at least one of the first and second members, and the actuating means includes a pin extending laterally through a cross bore in one bone portion and being rotatable to drive the gear means.

3. The adjustable fixation device specified in claim 2 wherein said drive means comprises a threaded member and a pair of intermeshing bevel gears driving said threaded member to move the first and second members relative to each other.

4. The adjustable fixation device of claim 1 wherein the means to fix the first and second members ralative to the respective bone portions comprises cross bores in the bone portions which are spaced from the bone interface, said first and second members each having bores aligning with the cross bore in the respective bone portion, one cross bore comprising the opening in said one bone portion, and pin means passing through the cross bores and the aligning bores in the respective first and second members to secure the first and second members to the bone portions, one pin means comprising part of the actuating means, said first and second members being controllable telescopically relative to each other.

5. The adjustable fixation device of claim 4 wherein the drive means comprises mating threads extending longitudinally along the first and second members, and wherein the actuating means comprises means to rotate one of the first and second members relative to the other comprising gear means, said one pin means being rotatable to drive the gear means.

6. The adjustable fixation device of claim 5 and mean to releasably lock said one pin means to selectively prevent rotation thereof.

7. A bidirectional fully bone implantable fixation device for securing together adjacent, separated bone portions having alignable longitudinal axes comprising:
    first and second members adapted to telescope relative to each other;
    means for forming longitudinal bores in the bone portions;
    said first member being adapted to be fitted into the bore in a first portion of a bone to be secured to the second portion of bone, and said second member being adapted to be fitted into the bore of a second bone portion, the bores in the respective bone portions each opening to an interface between the bone portions;
    drive means within the bone portions coupled between the first and second members so that upon driving motion of said drive means the first and second members will selectively move toward or away from each other in the direction of the longitudinal axes of the bone portions;
    frist means extending laterally from said first member adjacent an end thereof and adapted to be fitted through and substantially remain within a cross bore in the first bone portion and said first means comprising a rotary drive member for driving the drive means upon rotary movement thereof about an axis perpendicular to the axis of the respective bone portions, said rotary drive member being accessible from the exterior of the first bone portion; and
    second means extending laterally from said second member at an outer end thereof and adapted to be fitted through and remain substantially within a lateral cross bore in the second bone portion, the first and second means fixing the first and second members from longitudinal axial movement relative to the respective first and second bone portions with which they are associated.

8. The adjustable fixation device of claim 7 wherein said first and second means each comprise cross pins passing through bores in the first and second bone portions and through the first and second members, respectively.

9. The adjustable fixation device of claim 7 wherein the drive means is mounted within the first member, and comprises a threaded screw, said second member having a threaded bore for receiving the screw to control longitudinal movement between the two members, said rotary drive member having means to rotate said threaded screw.

10. The adjustable fixation device of claim 7 wherein said drive means comprises a first gear, and a second gear driven by rotation of the rotatable drive member of said first means and drivably engaging the second gear.

11. The adjustable fixation device of claim 7 wherein said first and second members telescope relative to each other, and are closely slidably fitted one within the other to provide stability against loads transverse to their longitudinal axis.

12. The adjustable fixation device of claim 11 wherein said rotary drive means comprises a rotary screw member rotatably mounted in said first member, a threaded bore in said second member for receiving said rotary screw member, and said rotary drive means further comprising gear means for rotating said screw member, said gear means being actuable upon rotary movement of said first means.

13. A method of adjustably fixing two bone portions relative to each other, said bone portions having longitudinally extending axes, and an interface formed between abutting end portions of the bone portions, comprising the steps of:

forming aligning longitudinal bores in the bone portions;

installing on each bone portion a drill guide fixture having a pin positioned in the longitudinally extending bore, and drill guide hubs fixed relative to the pin on the exterior sides of bone, and drilling at least one cross bore in each of the bone portions using the drill guide hubs so the cross bores are substantially perpendicular to the respective axes of the longitudinally extending bores;

placing separate first and second members having transverse end bores therethrough in the respective longitudinal bores and securing said first and second members from longitudinal movement relative to the respective bone portions, while permitting relative longitudinal movement between the first and second members by placing a cross pin through the cross bore in each bore portion and through aligning end bores of the respective first and second members; and providing means completely with the bone portions for moving said first and second members longitudinally relative to each other accessible from the exterior of the bone, and adjusting the relative longitudinal position of the first and second members to bring the interface between the two bone portions into abutment at a desired compression level.

14. The method of claim 13 including the steps of prividing a screw thread connection between the first and second members, and of providing one of the pin means with a gear positioned on the interior of said bone and engaging a gear on said first member and rotating the gears for driving the first member relative to the second member selectively to either extend or retract the first and second members.

* * * * *